(12) United States Patent
Hess

(10) Patent No.: US 6,825,323 B2
(45) Date of Patent: Nov. 30, 2004

(54) COMPOSITIONS FOR TREATMENT OF HEMORRHAGING WITH ACTIVATED FACTOR VIIA IN COMBINATION WITH FIBRINOGEN AND METHODS OF USING SAME

(75) Inventor: John R. Hess, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/756,907

(22) Filed: Jan. 10, 2001

(65) Prior Publication Data

US 2004/0198647 A1 Oct. 7, 2004

(51) Int. Cl.$^7$ .............................................. A61K 38/36
(52) U.S. Cl. ........................... 530/384; 514/2; 514/822
(58) Field of Search ....................... 514/2, 822; 530/384

(56) References Cited

U.S. PATENT DOCUMENTS

| | | |
|---|---|---|
| 5,504,067 A | 4/1996 | Morrissey et al. |
| 5,788,965 A | 8/1998 | Berkner et al. |
| 5,817,788 A | 10/1998 | Berkner et al. |
| 5,833,982 A | 11/1998 | Berkner et al. |
| 5,866,122 A | 2/1999 | Turecck et al. |
| 5,997,864 A | 12/1999 | Hart et al. |

OTHER PUBLICATIONS

Burnouf–Radosevich et al., "A therapeutic, highly purified factor XI concentrate from human plasma", 1992, Transfusion, 32(9), 861–867.*

Hedner U.: Treatment of patents with factor VIII and factor IX inhibitors with special focus on the use of recombinant factor VIIa.: Thromosis and Haemostasis: vol. 82, No. 2, 1999; pp. 531–539.

Schmidt M.L. et al.: Recombinant activated factor VII therapy for intracranial hemmrhage in hemophilia A patnets with inhibitors: american journal of hematology: vol. 47, No. 1, 1994, pp. 36–40.

* cited by examiner

Primary Examiner—Robert A. Wax
Assistant Examiner—Suzanne M. Mayer
(74) Attorney, Agent, or Firm—Elizabeth Arwine

(57) ABSTRACT

The combination of recombinant factor VIIa and fibrinogen is effective in treatment for bleeding where direct pressure, tourniquets, indirect pressure, surgical ligation, bandaging, and transfusion of blood or plasma products are typically used. The combination of factor VIIa and fibrinogen is administered intravenously, either sequentially or simultaneously. The compositions may be safely circulated in the blood vessels to sites of injury. This is effective for single or multiple external or internal wounds.

30 Claims, No Drawings

COMPOSITIONS FOR TREATMENT OF HEMORRHAGING WITH ACTIVATED FACTOR VIIA IN COMBINATION WITH FIBRINOGEN AND METHODS OF USING SAME

TECHNICAL FIELD

The invention relates to pharmaceutical compositions and methods of treatment that promote hemostasis, slow or stop internal and/or external bleeding at sites of blood vessel injury. The compositions contain factor VIIa and fibrinogen.

BACKGROUND ART

Hemorrhage is the most common cause of death among injured or treated individuals including those who die prior to reaching care, who die in emergency medical care, e.g. emergency room, or who die in the operating room (Holcomb J B, Pusateri A E, MacPhee M J, Hess J R. New technologies in hemorrhage control. Current Opinion in Critical Care. 1997 December; 3:488–493; Holcomb J B, Pusateri A E, Harris R A, Reid T J, Hess J R, MacPhee M J. Dry fibrin sealant dressings reduce blood loss and improve survival in hypothermic coagulopathic swine with grade V liver injury. J Trauma. 1999 August; 46:233–242). The most common causes of death of individuals in post-operative critical care are those involving sequellae of poorly controlled hemorrhage and shock. In the prehospital setting, most internal bleeding is not accessible for direct intervention. In the hospital setting, there are sources of bleeding which cannot be immediately controlled with the best surgical techniques, e.g. deep liver injuries with liver vein disruption, pelvic ring fractures with direct bone bleeding, pelvic venous plexus tears, etc.

Blood coagulation is a complex process that involves formation of a preliminary clot by platelets followed by a cascade of events involving several factors that eventually leads to strengthening of the clot. A critical step in this process is the production of thrombin, a proteolytic enzyme. This enzyme is involved in aggregation of platelets and in the activation of cleavage of fibrinogen into fibrin. Fibrin forms much of the stabilizing matrix for the platelet plug. Through a multistep cascade, various blood coagulation proenzymes and procofactors that circulate in the blood are sequentially or simultaneously converted to their activated forms (designated by a lower case "a", e.g. factor VIIa). The proenzymes are generally inactive and are converted to the active form by proteolytic enzymes present in the cascade. This cascade involves two separate multistep pathways which lead to the conversion of prothrombin to thrombin.

The first pathway is rapid and is known as the extrinsic pathway. This pathway involves the activation of coagulation factor VII to factor VIIa (Jack Hirsh and Elizabeth A. Brain, Hemostasis and Thrombosis-A Conceptual Approach. (2d ed. 1983)). Coagulant factor VII circulates in the blood at a concentration of 0.5 µg/ml plasma. The vast majority of circulating factor VII is inactive with about 1% of factor VII being in an active form. Activation of circulating factor VII requires exposure of factor VII to several cofactors. Factor VIIa, the active form, has little enzymatic activity until it complexes with tissue factor. Complex formation occurs at sites where the blood vessel endothelium is damaged or where underlying tissues, rich in tissue factor, is exposed, Also platelet activation exposes Factor VIIa to tissue factor that is normally stored internally in platelets. White blood cells will express tissue factor in response to inflammatory mediators and thereby cause the complex to be formed. Thus, seemingly large amounts of factor VIIa can circulate with little effect, but can be highly active at the requisite site by formation of the complex with tissue factor.

Activated factor VIIa converts factor X to factor Xa which in turn converts prothrombin to thrombin in the presence of the cofactors factor V, calcium ions and phospholipid.

The second, slower coagulation cascade is termed the intrinsic pathway and also involves factor VIIa as well. The intrinsic pathway comprises a series of reactions that leads to the activation of thrombin via activation of the Hageman factor (factor XII). This leads to the activation of factor XI which in turn results in the activation of factor IX in the presence of phospholipid. The activated factor IX (IXa), in the presence of factor VIII and phospholipid activates factor X, which cleaves prothrombin into the active form, thrombin. Factor VII is converted to the active form either by factor Xa in the presence of calcium and phospholipids, or by factor II (thrombin). In contrast to the extrinsic pathway, which leads to rapid blood coagulation at the point of injury, the intrinsic pathway strengthens the clot.

Factor VII has been purified and characterized as a single-chain glycoprotein of approximately 47,000 Daltons. It is converted to the active form by cleavage of an arginine-leucine bond which creates two chains held together by disulfide bonds (U.S. Pat. No. 5,504,067). Factor VIIa is more active than Factor VII by 100-fold. Efforts to use isolated factor VIIa in individuals with severe bleeding episodes have produced positive results, e.g. diminished blood loss of up to 50%. Recombinant factor VIIa has also been administered to individuals with various bleeding disorders, e.g. coagulation abnormalities with beneficial results.

Recombinant factor VIIa was also administered to a 19 year old Israeli soldier shot in the abdomen (Blauhut B. Indications for prothrombin complex concentrates in massive transfusions. Thromb Res 1999; 95(4 Supp 1):S63-9.). This patient arrived at the hospital in shock with a large paraspinal exit wound. Upon abdominal exploration, the patient was found to have multiple organ injuries and a laceration of the inferior vena cava. Surgeons rapidly repaired the injuries and tied off the inferior vena cava. At this point, the patient had received 40 units of blood. The patient was cold and coagulopathic, bleeding 300 ml/minute from soft tissue injuries. The surgeons thought the case was unsalvageable. However, upon administration of recombinant factor VIIa, the bleeding was immediately decreased to 15 ml/min, allowing surgeons to identify and the several more bleeding sites. A second dose of recombinant factor VIIa resulted in complete cessation of bleeding. Other conditions where beneficial results have been achieved include gastric ulcer bleeding from arterial erosion, thrombocytopathies, and children with dengue hemorrhage fever and shock.

A study (submitted for publication) was conducted involving recombinant factor VIIa as an adjunct to conventional liver packing for the treatment of a model of American Association for the Surgery of Trauma (AAST) grade 5 liver injury in swine rendered cold and coagulopathic by exchange transfusion of 60% of their blood volume with cold hydroxyethyl starch. This study examined the efficiency of factor VIIa on extreme cases where large amounts of blood loss have occurred and the patient is in trauma. It is well understood that patient chances of survival and quality of life will improve as blood loss is diminished. There was a 46% reduction in blood loss, which is a statistically significant decrease. The treatment corrected coagulopathy and caused no identifiable untoward effects.

Hemophilia is an excessive bleeding disorder due to the lack of one or more factors involved in the blood coagulation cascade. Hemophilia A is characterized by a lack of function associated with coagulation factor VIII, either through an absence of active factor VIIIa or inhibition of factor VIII.

Hemophilia B is characterized by an absence of coagulation factor IX. Both forms of hemophilia are associated with bleeding disorders potentially leading to severe injury or death. In the 1970's, hemophilia patients were sometimes treated with "active factor concentrates". These mixtures of the activated Vitamin K dependent factors (factors II, VII, IX, and X) were frequently effective in stopping hemophilic bleeding, but were associated with thrombotic side effects. Efforts to isolate the beneficial components in these mixtures culminated in 1982 with Hedner's isolation of factor VIIa in pure form from large volumes of plasma and her subsequent successful treatment of bleeding episodes in two patients with hemophilia A (Hedner U. Treatment of Patients with factor VIII and factor IX inhibitors with special focus on the use of recombinant factor VIIa. Thromb Hemost 1999; 82:531–539). Since then, more than 2400 bleeding episodes in more than 500 hemophilia patients have been treated with the recombinant protein. The expanded use of recombinant factor VIIa is now being incorporated into patients with various bleeding disorders, including platelet dysfunction syndromes and patients on anticoagulants.

A shortcoming of this treatment and others is that factor VIIa does not provide any of the material components of the clot itself. Unfortunately, the addition of factor VIIa alone in many instances is insufficient to produce clinically significant results. Factor VIIa can be rendered ineffective if supporting components are not present or are depleted from the system, either by a genetic deficiency or decreased concentration due to a medical condition.

Fibrin has been used as an administered blood coagulant as early as 1909 when wound scabs were dried, powdered, and sprinkled on wounds (Tock B, Drohan W, Hess J, Pusateri A, Holcomb J, MacPhee M. Hemophilia and advanced fibrin sealant technologies. Hemophilia 1998; 4:449–455.). Fibrinogen was isolated from human plasma in bulk quantities by Cohn during World War II, who made fibrin glues and fibrinogen concentrates for infusion. The use of fibrinogen or cleaved fibrin was stopped because the purification process would isolate hepatitis virus along with the fibrinogen and put individuals at risk for viral infection. The FDA removed the last human fibrinogen products from the market on Dec. 31, 1977. As a result, clinicians switched to using single donor blood products, fresh frozen plasma and cryoprecipitate as sources of injectable fibrinogen to treat severe surgical bleeding.

The human fibrinogen protein ordinarily circulates in the plasma at concentrations of 2–4 g/L plasma. In the uncleaved form, fibrinogen is inert in the bloodstream, and the activated form is not normally found in healthy blood vessels. Activation by thrombin occurs by cleavage of small activation peptides from the free ends of the paired $\alpha$ and $\beta$ chains. This converts fibrinogen to fibrin monomer by exposing "sticky" ends on the fibrin monomeric units. The polymer can be formed by building a matrix from fibrin monomers. Fibrin binds to collagen and receptors on platelets, anchoring it to tissue in wounds and the other components of the clot. Adherent clot begins to form at the edge of the wound and builds a mass of adherent clot which grows toward the center of the wound, recruiting platelets which form the basis for new activation sites.

Because fibrin is a structural protein, its effect is a direct function of the amount present. A correlation between fibrinogen content and clot strength has been reported. (Holcomb J B, Harris R A, MacPhee M J, Charles N C, Beall L D, Hess, J R. Effect of fibrin bandage fibrinogen concentration on blood loss after grade V liver injury in swine. Mil Med, accepted for publication). The concentration of fibrin in injured vessels is a direct function of the rate of production from fibrinogen and the rate of loss through the wound or from breakdown. The rate of fibrin production is a function of the thrombin enzyme activity and of the concentration of the fibrinogen substrate. Thus, when a wound is formed that breaks a blood vessel, blood is exposed to tissues which activate the coagulation system. Activation starts the clotting at the edge of the wound and builds a mass of adherent clot which grows toward the center of the wound by recruiting platelets which form the basis for new activation sites and tying them to the wound edge with fibrin. As long as the strength of the clot and its adherence to the wound edge are greater than the other forces operating on the wound such as blood pressure, the clot continues to grow and progressively occludes and seals the wound. This basic coagulation mechanism works well in small wounds, poorly in large arterial disruptions, and performs variably for wounds of intermediate severity.

All publications cited herein, including patent applications, are hereby incorporated by reference in their entirety.

DISCLOSURE OF THE INVENTION

The present invention includes compositions of factor VIIa and fibrinogen and methods of using these compositions to minimize or stop traumatic bleeding at internal and/or external wound sites by activating the blood clotting system at sites of injury. The composition may be used in the field. This should allow more individuals to reach the hospital alive with more of their own blood, thus minimizing the need for transfusions of plasma. This will also minimize the risk of introducing detrimental foreign agents and also economize the therapeutic benefit.

It is an object of the present invention to provide compositions and methods for treatment of bleeding episodes, such as hemorrhaging, hemophiliac bleeding and excessive bleeding due to platelet disorders. It is a further object of the present invention to provide compositions and methods for the therapy of individuals with blood clotting deficiencies. It is a further object of the present invention to provide compositions and methods for the therapy of individuals with bleeding disorders. The composition of the present invention can decrease blood loss and is easily transportable for use in remote locations.

Accordingly, in one aspect, the present invention provides compositions comprising factor VIIa and fibrinogen. Activated factor VIIa is capable of catalyzing the blood cloning cascade at sites of injury by facilitating the cleavage of fibrinogen to fibrin monomers that are used to build up the clot. In a preferred embodiment, factor VIIa is recombinantly produced to efficiently manufacture large quantities of factor VIIa while minimizing the risk of contamination. Activated factor VIIa is only functional at sites of blood vessel injury where there is exposure of tissue factor and factor VIIa will rapidly activate the coagulation cascade. In another preferred embodiment, fibrinogen is recombinantly produced to efficiently manufacture large quantities of fibrinogen while minimizing the risk of contamination. In a related aspect, the compositions of the present invention further contain one or more stabilizing agents. The compositions may be injected into the bloodstream of the individual where they can circulate to sites of injury. In some embodiments, the compositions are dissolved in a proper excipient for infusion. In other embodiments, the compositions are lyophilized for long term storage and ease of transportation.

Another embodiment relates to kits. A kit format would facilitate the use of factor VIIa and fibrinogen in a variety of situations, including those where immediate hospitalization is not possible or delayed, e.g., natural disasters, military combat locations, rural settings. The active components can be placed together or separately in one or more containers.

In addition, the kits may include other items or materials which would be associated with a desired application including any excipient required for injection of factor VIIa and fibrinogen, device for injection (e.g. syringe), tourniquet, and alcohol cleaning packet. It is also contemplated that the fibrinogen, factor VIIa and any other sensitive active component or otherwise would be placed in a form and/or include materials which would promote stability of the compounds during storage including those which prevent microbial contamination. If the active materials are not in a form permitting direct use, the kit could include materials which aid in the conversion of the active ingredients to injectable form. Also, if desired, additional factors that may aid in the function of coagulation may be included. The kits also allow for convenient storage and transportation of the invention to remote locations.

In another aspect, the present invention provides methods for treating individuals with excessive bleeding. In a related aspect, the present invention provides methods for enhancing blood coagulation. In one embodiment, the present invention is used in individuals with mild to severe bleeding due to any variety of causes, including but not exclusive to: open wounds, liver hemorrhaging, hemophiliac bleeding episodes, bleeding disorders and blood clotting deficiencies. In a further embodiment, the present invention is administered to individuals in an amount effective to cause hemostasis. In yet a further embodiment, the present invention may be administered multiple times to cause hemostasis or to decrease bleeding.

The present invention includes effective formulations for treating hemorrhaging (i.e. induce coagulation, decrease bleeding, control bleeding, seal wounds). Each component is included in the composition in quantities sufficient to promote hemostasis. Factor VIIa is included in quantities to increase the amount of activated factor VIIa at sites of injury and promote the catalysis of clot formation. Fibrinogen is included in quantities to support maintenance of a circulating supply of clotting material.

MODES FOR CARRYING OUT THE INVENTION

The invention provides pharmaceutical compositions and methods for controlling bleeding, blood coagulation, and wound sealing. The composition comprising factor VIIa and fibrinogen effectively serves to activate the rapid blood coagulation factor cascade and provide the necessary components for strong clot formation. While introduction of these two factors is beneficial to hemostasis through decreasing blood clotting times, the benefit to the individual is also seen in the diminished blood loss, resulting in less cold transfusions and healthier individuals which translates into faster healing times. Also, rapid blood clotting means less blood loss into the local wound hematoma, meaning less blood to resorb and fewer complications, such as infection.

The coagulation combination of factor VIIa and fibrinogen may be injected into the bloodstream without putting individuals at high risk for blood vessel occlusion. The two components may be injected simultaneously or sequentially or at multiple sites to enhance delivery and/or effect depending on the situation. The activity of the components is dependent upon the components of the present invention circulating to the sites of injury. Since the factors are free to circulate in the bloodstream, they can be effective in hemostasis, or clot formation, or decreasing bleeding at multiple sites of injury. Because the components of the composition circulate to the sites of injury, the sites of injury do not have to be specified prior to administering treatment.

The combination of recombinant factor VIIa and fibrinogen is effective in cases of moderate and severe bleeding or wound sealing where direct pressure, tourniquets, indirect pressure (e.g. liver packing), surgical ligation, bandaging, and transfusion of blood or plasma products are typically used. Other methods previously used to induce coagulation (e.g. estrogen) or inhibit fibrinolysis (e.g. aprotinin) are effective for small wounds, but not effective in large vessel hemorrhage. The combination of factor VIIa and fibrinogen is administered intravenously, and the compositions are circulated to sites of injury. This is especially effective for multiple wounds, especially in cases where bleeding from damaged vessels is obstructive to treatment and observation and can complicate location of the bleeding sources, inaccessible internal bleeding and individuals with prolonged bleeding. This also saves time in treatment by not having to localize injury sites prior to treatment. The use of these two administered blood coagulation components can reduce bleeding by 50% or more, and can cause complete cessation of bleeding in as little as one administration.

Other conditions that can be treated with the combination of the present invention include use in surgery (e.g. central line incisions, atrioventricular shunts), surgical bleeding from the microvasculature, postoperative bleeding episodes, clinical procedures (e.g. needle biopsies), prophylactic administration during clinical procedures, dental procedures, surgery or procedure that is contraindicated in high risk individuals (e.g. cirrhosis patients) and platelet dysfunction. Also, the combination is useful in situations where stabilization of an individual may have a negative effect on the bleeding of the individual, including attempts at resuscitation, temporal factors associated with stabilizing an individual in an emergency room, and a "bloody vicious cycle" where care givers attempt to correct anatomy in the operating room, leading to long operations which result in more bleeding, more resuscitation with more hypothermia and dilutional coagulopathy leading to increased bleeding. The effect of administration of this combination is that it will extend the golden hour and save lives and limbs in trauma cases, military/combat related events where medical attention is removed, severe hemorrhaging (e.g. liver), stabilization of an individual (such that proper diagnosis may be performed). In addition, the increased ability to promote hemostasis minimizes necessity for blood product transfusions and reduces the need for tourniquets, effectively saving limbs.

Definitions

As used herein, a "recombinant" protein include those proteins made by recombinant techniques. These proteins include those which resemble the natural protein as well as those modified to enhance activity, protein half-life, protein stability, protein localization and protein efficacy.

An "individual" is a vertebrate, preferably a mammal, more preferably a human. Mammals also include, but are not limited to, farm animals, sport animals and pets.

An "effective amount" is an amount sufficient to offer beneficial or desired clinical results. An effective amount can be described in individual amounts, such as the quantity injected (e.g. 3 g fibrinogen material), or as the desired relative amounts (e.g. 160 IU/kg body weight). An effective amount can be administered in one or more administrations. For purposes of this invention, an effective amount of factor VIIa and fibrinogen is an amount that is sufficient to cause hemostasis, clot formation, decrease bleeding, blood coagulation, or decrease blood loss.

As used herein, "hemostasis" is the arrest of bleeding, involving the physiological process of blood coagulation at ruptured or punctured blood vessels and possibly the contraction of damaged blood vessels.

As used herein, "treatment" is a method for obtaining beneficial or desired clinical results. For purposes of this invention, beneficial or desired clinical results include, but are not limited to, alleviation of symptoms, diminishment of bleeding, stabilization of the individual, preventing bleeding. "Treatment" can also mean prolonging survival of the individual.

As used herein, "bleeding disorder" is defined as decreased ability to control bleeding due to one of the following: vascular defects, thrombocytopenia, thrombocytopathia, defects in blood coagulation or excessive fibrinolytic activity.

Combination of Factor VIIa and Fibrinogen

The pharmaceutical combination of the present invention is used to cause hemostasis, wound sealing, blood clotting, decrease of blood loss or help effect blood coagulation. The pharmaceutical combination of the present invention can be manufactured and kept stable in a variety of dry and wet forms. The dry powders or the liquid solutions can be mixed, sterilely packaged, and stored for years dry or months wet. Both proteins are isolated by chromatography in essentially pure form at the end of production. Thus, the use of this pharmaceutical combination is safer than administering fresh frozen plasma, since it eliminates complications associated with other blood products (e.g. blood typing, foreign matter, viral contaminants). Other ingredients may be added for stability of the two components, such as sugars, polysaccharides, such as low molecular weight dextrans, polyalcohols such as glycerol, and antioxidants, such as bisulfite or ascorbate, which act as stabilizers during the lyophilization process, or vitamin K or albumin. Vitamin K is an essential element for factor VIIa activity and albumin has been shown to act as a stabilizer for factor VIIa activity. The stabilizing agents are generally present in a concentration from 0.1 to 5% weight/volume. The combination can be rehydrated easily in solution with appropriate excipients, such as but not limited to sucrose solution, saline or distilled water. Each excipient rapidly dissolves the components of the composition. The two proteins have no significant chemical or physical interactions in solution. The composition may be reconstituted and administered by a medic, corpsman, or medical staff member and use in remote settings is possible.

In some embodiments, one or both of the components of the present invention may be recombinantly produced or modified. A recombinant or modified form of either protein retains the functional characteristics of the native protein. The native activity may be assessed by a prothrombin assay to determine the effectiveness of the protein on blood coagulation time. The dosage of the components of the present invention depend upon the clinical situation including, but not limited to factors such as the inhibition or deficiency of clotting factors, the locations and severity of the hemorrhaging and the general physical condition of the individual. The dosage must be empirically evaluated by the clinician in their assessment of the most beneficial therapy for the individual. The components of the present invention may be administered sequentially or simultaneously. In most cases, the administration amount of factor VIIa is sufficient to produce a concentration of about up to 300 IU/kg body weight, preferably 25–250 IU/kg body weight, more preferably 50–200 IU/kg body weight, even more preferably 60–180 IU/kg body weight, although factor VIIa can be administered at higher concentrations if the situation warrants. One IU is the amount of factor VII and factor VIIa that circulates in 1.0 mL plasma of a normal person. The administration amount of fibrinogen is about up to 12.0 g/L plasma, preferably 0.25–10.0 g/L plasma, more preferably 0.5–6.0 g/L plasma, although fibrinogen can be administered at higher quantities if the situation warrants.

The administration of the composition of the present invention has activity from between 8–12 hours. An individual who has a bleeding episode may be reassessed and readministered the composition if bleeding has not decreased to an acceptable level. An acceptable level is defined as bleeding that is controlled and does not pose any threat to the life of the individual or cause any detrimental harm to the individual. The composition may be administered at time intervals much shorter than 8–12 hours, and may be as little as 0.5–2 hours. It must be noted that the components of the present invention have a limited biological half-life, which may factor into the frequency of administration. Thus, it may be beneficial to administer smaller doses more frequently. The composition of the current invention may be administered by bolus injection or by continuous infusion; the method of administration should be reflective of the purpose of administration. For example, if there is severe bleeding and complete or partial coagulation or decrease in bleeding is desired, a bolus injection would be preferred. In cases of prophylactic use, such as during controlled minor surgical procedures, a method of continuous infusion may be used.

The activation of factor VIIa leads to an approximate 100-fold amplification of thrombin formation, leading to the initiation of blood coagulation at the site of injury. Coupled to the increase in thrombin production is an increase in activity of platelets, resulting in an increase of platelet activation by 10,000-fold. Platelet activation results in further activation of the coagulation cascade and adhesion of platelets to the site of injury. The combination of activated coagulation factors results in an overall synergistic effect on blood coagulation by 1,000,000-fold.

In some embodiments the invention can be assembled into a kit. The kit would contain both components, factor VIIa and fibrinogen, as well as any necessary excipients, such as but not limited to saline and sucrose solution, and any additional factors for stabilization or effectiveness of the components of the composition, such as, but not limited to sugars, antioxidants, vitamin K, and albumin. Sugars and antioxidants act as stabilizers during the lyophilization process. In addition, the kit may comprise other elements involved in the delivery of the composition, including a device for injection of the composition of the current invention (e.g. syringe), tourniquet, and alcohol swab to clean the site of injection. Other elements may also be included in a kit including elements involved in wound closure such as suture material, needles and forceps. Having the present invention in a kit form would allow mobile use of the invention in locations not amenable for full hospital facilities.

The present invention is useful for states of bleeding, including traumatic hemorrhaging, inaccessible internal injuries, or individuals with bleeding episodes who have blood disorders.

Both elements of the present invention have excellent safety profiles. Hundreds of individuals get recombinant factor VIIa and tens of thousands receive fibrinogen in the form of blood products each day. Both components of the present invention are well characterized proteins that have been characterized in terms of distribution, metabolism, and excretion. The two components are not known to have any metabolic interference between the components or effects on clearance between the components or with other drugs to any significant extent that are likely to be used in subsequent surgical and medical care of the typical trauma victim.

Factor VIIa

Factor VIIa is defined as a polypeptide of about 47,000 Daltons and is involved in the coagulation cascade. Factor VIIa is further defined as any whole factor VIIa polypeptide or functional equivalent, including but not limited to deletions, insertions, mutations, modifications, truncations and transpositions of amino acids from the polypeptide sequence. The functionality of factor VIIa or a functional equivalent may be tested by administering a prothrombin assay. The prothrombin assay is commonly used in the art to determine effectiveness of a component to coagulate blood. The prothrombin assay is performed by adding tissue extract and calcium to plasma and added factor VIIa or a putative functional equivalent. This will initiate clotting in a functional system and if the added factor VIIa or putative functional equivalent is functional, then the coagulation time should decrease with respect to a control sample in which factor VIIa or a putative functional equivalent was not added.

Factor VIIa can be prepared as previously described (Fair et al., 1983). The factor VIIa protein can be recombinantly produced or modified as well. The essential difference between the recombinant factor VIIa protein and non-recombinant factor VIIa protein is that a recombinant factor VIIa protein is produced by recombinant techniques. The protein may be modified in a number of ways, including but not limited to chemical modification, glycosylation, methylation, hydroxylation, amino acid deletion, insertion, mutation, truncation and transposition. A recombinant form of factor VIIa will still retain the functional characteristics of native factor VIIa. The functionality of the recombinant protein may be tested using a prothrombin assay to determine the effectiveness of the protein on blood coagulation time. The benefit of using the recombinant activated form is that large quantities can be safely, effectively and economically produced. The amino acid sequence of factor VII (Hagen et al., 1986) is converted to the mature form by removing the leader sequence of 60 amino acids and activation occurs by cleavage of a peptide bond between arginine-212 and isoleucine-213. This cleavage may be accomplished in vitro by incubation of the factor VII protein with factor Xa. Alternatively, recombinant factor VIIa is commercially available from Novo Nordisk (Bagsvaerd, Denmark). The administration dose of factor VIIa is effective to produce in the plasma an effective level of about up to 300 IU/kg body weight, preferably between 25–250 IU/kg body weight, more preferably between 50–200 IU/kg body weight, even more preferably between 60–180 IU/kg body weight, although factor VIIa may be administered in higher concentration. It is known that an average individual has about 40 mL of plasma per kilogram of body weight and that in normal circulation, there is about 1 IU factor VII and factor VIIa per milliliter of plasma. Thus, there is about 40 IU/kg body weight with 99% being the inactive factor VII form. Addition of 180 IU/kg body weight of activated factor VIIa would yield a total of about 220 IU/kg body weight, of which 82% would be the active factor VIIa form. Increasing the administration to 300 IU/kg results in 88% of circulating factor VII being the active factor VIIa form. Thus, while the concentration may be increased beyond 300 IU/kg body weight, there is a diminishing return on increased percentage of active factor VIIa. Albumin or other stabilizing agents present should be at a concentration from about 0.1–5% weight/volume.

It is a necessary aspect of the invention that factor VIIa is in an activated form. Normal circulating levels of factor VIIa represent only 1% of circulating factor VII. The activated factor VIIa must compete at sites of injury with the inactive factor VII for binding to tissue factor. By introducing additional quantities of factor VIIa, the likelihood of factor VIIa binding to tissue factor, as opposed to inactive factor VII binding tissue factor may be increased from 1% to 25%, preferably 50%, more preferably 60%, 70%, or 80% or greater.

The administration of factor VIIa may be of benefit for individuals suffering from a bleeding episode, including those with brain injury. Brain has the highest concentrations of tissue factor in the body (Bouchard B A, Shatos M A, Tracy P B. Human brain pericytes differentially regulate coagulation. Atherioscler Thromb Vasc Biol 1997; 17:1–9). The only clinical experience is in individuals with hemophilia who occasionally bleed into their head. Treatment with recombinant factor VIIa has reduced the mortality of this complication from 50% to 8%. Its effect on individuals with normal coagulation is not known.

Human Fibrinogen

The human fibrinogen protein ordinarily circulates in high quantities in plasma (2–4 g/L). Fibrinogen acts as a plug substrate for sealing vessel injury sites. At times of injury, the body is stimulated to produce excess amounts of fibrinogen. The activation response to produce increased quantities of fibrinogen produces levels of fibrinogen 2–3 times the normal level. This upregulation and production of fibrinogen takes approximately 1–2 days, at which time large quantities of blood loss may have already occurred. This delayed process is often ineffectively late in cases of severe bleeding or bleeding at critical sites. Introduction of fibrinogen will increase the concentration of fibrinogen in the plasma in a shorter time period. Thus, the introduction of excess fibrinogen will allow the extrinsic coagulation pathway to occur without being hindered by a lack of fibrinogen working material. Use of plasma and blood products have been used to replenish the diminished supply of fibrinogen in the past. A single dose of 3–10 grams of fibrinogen is equivalent to the fibrinogen content of 10–25 units of fresh frozen plasma or cryoprecipitate.

Fibrinogen is further defined as any whole fibrinogen polypeptide or functional equivalent, including but not limited to deletions, insertions, mutations, modifications, truncations and transpositions of amino acids from the polypeptide sequence. The functionality of fibrinogen or a functional equivalent may be tested by administering a prothrombin assay to determine the effectiveness of the polypeptide on blood coagulation time.

It is now possible to manufacture injectable fibrinogen solutions which are virus-free. Fibrinogen may be produced by bulk purification from plasma and followed by further purification with detergent treatment or other means to inactivate contaminants such as viral contaminants, for example Hepatitis virus particles. Alternatively, fibrinogen is commercially available from multiple companies (e.g. Baxter, Alpha Therapeutics). Alternatively, fibrinogen may be recombinantly produced. The essential difference between the recombinant fibrinogen polypeptide and non-recombinant fibrinogen polypeptide is that a recombinant fibrinogen polypeptide is produced by recombinant techniques. The fibrinogen polypeptide may be modified in a number of ways, including but not limited to chemical modification, glycosylation, methylation, hydroxylation, amino acid deletion, insertion, mutation, truncation and transposition. A recombinant form of fibrinogen polypeptide will still retain the functional characteristics of native fibrinogen polypeptide. The functionality of the recombinant protein may be tested using a prothrombin assay to determine the effectiveness of the polypeptide on blood coagulation time. The essential difference between recombinant fibrinogen and non-recombinant fibrinogen is that recombinant fibrinogen does not occur in nature, or contains elements or modifications not normally found in nature. The benefit of using the recombinant activated form is that large quantities can be safely, effectively and economically produced.

Fibrinogen is relatively less soluble than some other plasma proteins. 10% solutions (1 g/10 mL) are feasible, whereas solutions above 15% are viscous and difficult to rehydrate. Attempts at modifying fibrinogen have resulted in decreased solubility. A normal individual weighing 70 kg has about 3 liters of plasma volume each containing 2–4 g/L of fibrinogen. A dose of 3 grams, which would insure the minimum plasma fibrinogen concentration of 1 g/L and raising the plasma concentration by 25–50% can be formulated and administered in as little as 30 mL. Fibrinogen may be administered in a dosage effective to produce in the plasma an effective level of about up to 12.0 g/L, preferably 0.25–10.0 g/L, more preferably 0.5–6.0 g/L, although fibrinogen may be administered in higher quantities. Factors that may be involved in determining the amount of fibrinogen administered include the amount of fibrinogen suspected to be lost through bleeding, the number and severity of hemorrhaging sites, and the location of injection(s). For example, higher overall fibrinogen quantities may be achieved by multiple injections of 6.0–12.0 g injections near multiple sites of hemorrhaging injury.

Safety considerations regarding the administration of blood products have previously prevented the administration of blood products to individuals with plasma fibrinogen concentrations greater than 1 g/L. The clinical argument is that bleeding in individuals with plasma concentrations for fibrinogen greater than 1 g/L indicates a surgical, rather than coagulopathic matter. This has been found to not necessarily be the case and it may be advantageous to administer the clot forming substrate fibrinogen, especially in individuals who have been bleeding profusely and have diminished quantities of fibrinogen. Likewise, safety precautions prevent the administration of activated fibrin, which may form unwanted thrombi within blood vessels at random locations.

Administration of the Combination of Factor VIIa and Fibrinogen

The combination of the present invention is administered by infusion using a pharmaceutically acceptable carrier such as, but not limited to, simple sugar solutions, saline or buffered saline. Factor VIIa is administered in a dosage effective to produce in the plasma an effective level of about up to 300 IU/kg body weight, preferably between 25–250 IU/kg body weight, more preferably between 50–200 IU/kg body weight, even more preferably between 60–180 IU/kg body weight. Fibrinogen is administered in a dosage effective to produce in the plasma an effective level of about up to 12.0 g/L, preferably 0.25–10.0 g/L, more preferably 0.5–6.0 g/L plasma.

Intravenous injection of the two components, factor VIIa and fibrinogen, is a safe means of administration that allows the two components to circulate to sites of blood vessel injury. The composition of the present invention may be injected in a bolus injection or through continuous infusion. The two components are active only at locations of vessel damage and can be effective at multiple injury sites, including internal wounds that are inaccessible, or combinations of internal and external hemorrhaging, or injuries that can only be treated by packing (e.g. liver hemorrhaging). None of the components of the invention is thrombotic in normal vessels. Recombinant factor VIIa is only effective at locations where the endothelium has been breached and the factor VIIa protein is accessible to tissue factor. Factor VIIa circulates with a relatively long half-life, about 8–12 hours in plasma. Fibrinogen can only be converted to the matrix forming fibrin following a series of events involving factor VIIa at sites of injury. This combination activates factors IX and X to activate thrombin which breaks down fibrinogen to form fibrin monomer. Factor IX, X and thrombin (factor II) cannot be injected due to the significant risk of causing intravessicular blood clots. Activated factor VIIa is 100 times more functional in the presence of tissue factor, which is exposed at blood vessel injury sites. This means that the combination is preferentially active at sites of injury, where it is needed for hemostasis, or wound sealing, or decreasing bleeding or blood coagulation.

The following examples are provided to illustrate but not limit the invention.

EXAMPLES

Example 1

External Hemorrhaging at a Remote Field Location

An individual suffering multiple external injuries in a combat field situation cannot be immediately transported to a hospital. The medic attempts to minimize bleeding in order to maximize the chances of bringing the patient to a medical care facility alive. Initial treatment includes pressure on the wounds and fibrin sealants to slow the bleeding. The individual does not experience sufficient decrease in bleeding and an injectable blood coagulation kit of the present invention is utilized. The kit includes a vial with the components of the invention in the following amounts: 10,000 U lyophilized factor VIIa and 3 g lyophilized fibrinogen. A second vial contains 100 ml purified 5% saline solution. Using a syringe included in the kit, 30 ml of saline is mixed with the factor VIIa and fibrinogen and shaken until the factor VIIa and fibrinogen are in solution. The entire solution is injected intravenously into the arm of the patient where it can circulate to sites of injury. The patient is reassessed for bleeding following 30 minutes observation, and if bleeding has not decreased to a controllable level, then a second injectable blood coagulation kit may be opened and administered.

Example 2

Internal Hemorrhaging and Liver Injury

Individual presents at hospital with multiple internal and external injuries following an automobile accident. Among the injuries is liver hemorrhaging that can only be treated with liver packing and internal hemorrhaging sites that are not accessible. Other hemorrhage sites are difficult to ascertain due to the amount of bleeding present. Direct pressure is applied to the exposed wounds, and major bleeding vessels are cauterized as they are located. Large amounts of blood loss are occurring and several major vessels still cannot be localized due to the excessive blood pooling. A vial of premixed factor VIIa and fibrinogen, containing 15,000 IU factor VIIa and 3 g fibrinogen in a 30 ml 5% sucrose solution is injected intravenously into an accessible intact vein. The patient is assessed for excess bleeding after 30 minutes and appropriate action taken including readministration of the present invention, and either blood or plasma transfusion, as assessed by the health care professional.

Example 3

Surgical Prophylaxis for Patients with Coagulation Diminishing Pathologies

Individual requiring surgical intervention has cirrhosis and as a result, decreased levels of both factor VII and fibrinogen. It is understood that typical surgical procedure will warrant some blood loss in normal patients, but presents an unusually high risk in an individual with a blood clotting disorder. Individual is placed on a continuous infusion of 5% sucrose solution in which the composition of the present invention is included. The amount of factor VIIa is 5,000 IU/L solution and the amount of fibrinogen is 5.0 g/L solution. The mixture is administered in a continuous drip at an empirically determined rate starting 1 hour prior to surgery and continuously administered until 1 hour post surgery. Injection of higher amounts of the composition of the current invention is possible throughout the surgical procedure if abnormally high amounts of blood loss occur.

Example 4

Use in Individuals with Blood Disorders

In the platelet disorder Glantzman's thrombesthenia, platelets contract poorly resulting in weak clots and severe bleeding episodes. However, the platelets do stick at the injury site, express tissue factor, and provide a site for the assembly of the pro-X-ase (factors VIII and IX) and pro-thrombinase (factors X and V) enzyme complexes. The individual present with a bleeding episode with multiple hemorrhaging sites. Addition of excess amounts of recombinant factor VIIa and fibrinogen will stop the bleeding in Glantzman's thrombesthenia, not by correcting the platelet defect, but by "overdriving" the plasma coagulation protein system. Treatment of the individual is performed using direct pressure at the sites of bleeding and an effective amount of the composition of the present invention. An intravenous injection of 15,000 IU of factor VIIa and 3 g fibrinogen in 50 mL saline is injected and the patient is assessed for continued bleeding at 30 minutes post injection.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A pharmaceutical composition consisting essentially of functional factor VIIa and fibrinogen in a pharmaceutically acceptable carrier.

2. The composition of claim 1 wherein the amounts of said functional factor VIIa and said fibrinogen are effective to facilitate blood coagulation at sites of blood vessel injury.

3. The composition of claim 1 wherein the composition is free of other blood clotting factors.

4. The composition of claim 1 wherein the effective amount produces a hemostatic effect.

5. The composition of claim 1 wherein said factor VIIa is recombinantly produced.

6. The composition of claim 1 wherein said fibrinogen is recombinantly produced.

7. The composition of claim 1 further comprising a stabilizing agent.

8. The composition of claim 1 wherein said carrier is water, saline, buffered saline or sucrose solution.

9. The composition of claim 1 wherein the concentration of said factor VIIa is sufficient to produce an administered amount of up to about 300 IU/kg body weight.

10. The composition of claim 1 wherein the concentration of said fibrinogen is sufficient to produce an administered amount of up to about 12.0 g/L plasma.

11. The composition of claim 1 wherein the concentration of said factor VIIa is up to about 20,000 IU/10 mL.

12. The composition of claim 1 wherein the concentration of said fibrinogen is up to about 1 g/10 mL.

13. The composition of claim 1 wherein said composition is lyophilized.

14. The composition of claim 13 wherein the composition is reconstituted in a proper excipient to a concentration of about up to 20,000 IU/10 mL for said recombinant factor VIIa and up to about 1 g/10 mL for said fibrinogen.

15. A method for treating an individual having a bleeding condition comprising administering to the individual the composition of any one of claims 1 to 14.

16. The method according to claim 15 wherein the individual has a blood clotting deficiency.

17. The method according to claim 15 wherein the individual has a traumatic injury which causes bleeding.

18. The method according to claim 15 wherein the individual is undergoing a surgical procedure.

19. The method of claim 15 wherein the administered amount of said factor VIIa is about up to 300 IU/kg of body weight.

20. The method of claim 15 wherein the administered amount of said fibrinogen is about up to 12.0 g/L plasma.

21. The method of claim 15 wherein the composition is administered by continuous infusion.

22. The method of claim 15 wherein the composition is administered by bolus injection.

23. The method of claim 15 wherein said factor VIIa and said fibrinogen may be administered sequentially or simultaneously.

24. The method of claim 15 wherein the concentration of said factor VIIa is about up to 300 IU/kg body weight and the concentration of said fibrinogen is up to about 12 g/L plasma.

25. A kit for blood coagulation comprising factor VIIa, fibrinogen, a pharmaceutically acceptable carrier, and a device for administration of the composition, wherein factor VIIa and fibrinogen are present in amounts effective for treating an individual in one or more administrations.

26. A kit for blood coagulation according to claim 25 wherein the factor VIIa and fibrinogen are separately contained.

27. A kit for blood coagulation according to claim 25 wherein one or both factor VIIa and/or fibrinogen are in a dry or lyophilized form.

28. A kit for blood coagulation according to claim 25 wherein one or both factor VIIa and/or fibrinogen are in solution.

29. A kit for blood coagulation according to claim 25 wherein the kit includes one or more stabilizing agents along with factor VIIa and/or fibrinogen.

30. A kit for blood coagulation according to claim 25 wherein said device for administration is suitable for intravenous administration.

* * * * *